United States Patent [19]

Bakel

[11] Patent Number: 4,486,356
[45] Date of Patent: Dec. 4, 1984

[54] PROCESS FOR PRODUCING N-PHOSPHONOMETHYLGLYCINE DERIVATIVES

[75] Inventor: Izhak Bakel, Ramat Gan, Israel

[73] Assignee: Geshuri Laboratories, Ltd., Tel-Mond, Israel

[21] Appl. No.: 485,501

[22] Filed: Apr. 15, 1983

[30] Foreign Application Priority Data

Jun. 25, 1982 [IL] Israel ................................. 66137
Sep. 17, 1982 [IL] Israel ................................. 66824

[51] Int. Cl.$^3$ .............................................. C07C 9/38
[52] U.S. Cl. ........................ 260/501.12; 260/502.5 F
[58] Field of Search ................ 260/501.12, 502.5 F

[56] References Cited

U.S. PATENT DOCUMENTS

| | | | |
|---|---|---|---|
| 3,853,530 | 12/1974 | Franz | 260/501.12 |
| 3,950,402 | 4/1976 | Franz | 260/502.5 F |
| 3,954,848 | 5/1976 | Franz | 260/502.5 F |
| 3,969,398 | 7/1976 | Hershman | 260/502.5 F |
| 3,977,860 | 8/1976 | Franz | 260/502.5 F |
| 4,147,719 | 4/1979 | Franz | 260/501.12 |
| 4,148,624 | 4/1979 | Maier | 260/502.5 F |
| 4,397,676 | 8/1983 | Bakel | 260/501.12 |

*Primary Examiner*—Glennon H. Hollrah
*Assistant Examiner*—Raymond Covington
*Attorney, Agent, or Firm*—Cushman, Darby & Cushman

[57] ABSTRACT

The invention provides a process for producing water-soluble mono and di-N-Phosphonomethylglycine amine and iminourea salts from N-phosphonomethyliminodiacetic acid derivatives comprising oxidizing an aryl substituted iminourea salt of N-phosphonomethyliminodiacetic acid of the general formula VI

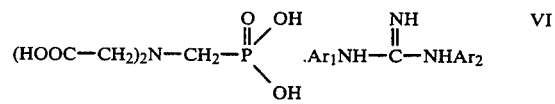

wherein Ar$_1$ and Ar$_2$ are each independently selected from the group consisting of phenyl, alkylphenyl and halophenyl to form a N-phosphonomethylglycine iminourea salt of the general formula VII

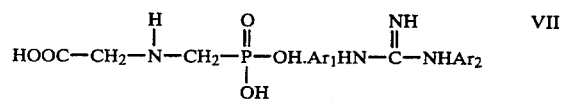

reacting the salt of formula VII with an amine, iminourea, diamine, or diiminourea having a molecular weight below 600 and a pKa above 10 in aqueous solution and separating the resulting water insoluble aryl iminourea from the resulting water soluble N-phosphonomethylglycine salt product. The invention also provides herbicidal N-phosphonomethylglycine compounds and compositions prepared by the above process.

7 Claims, No Drawings

PROCESS FOR PRODUCING N-PHOSPHONOMETHYLGLYCINE DERIVATIVES

The present invention relates to a new direct process for preparing various water soluble salts of N-phosphonomethylglycine (NPMG) from N-phosphonomethyliminodiacetic acid (NPMIDA) derivatives.

More particularly, the present invention relates to a process for producing water-soluble mono- and di-NPMG amine and iminourea salts.

As disclosed in U.S. Pat. No. 3,799,758 and as described in Israel Specification Nos. 65187, 66402 and 66494, the teachings of which are incorporated herein by reference certain amine, diamine, iminourea and diiminourea salts can be used as broad spectrum herbicides having little or no residual effect.

U.S. Pat. No. 3,799,758 describes the preparation of amine salts by neutralization of N-Phosphonomethylglycine (NPMG) with amines. In this process one needs to isolate pure NPMG by various methods known in art. Thus, e.g., pure NPMG can be produced by oxidation of NPMIDA using concentrated $H_2SO_4$ (Israeli Pat. No. 41842), $H_2O_2$ with concentrated $H_2SO_4$ (Israeli Pat. No. 42393) and $O_2$/catalyst (Israeli Pat. No. 47202). In the first and second methods great excess of $H_2SO_4$ is also needed to dissolve the NPMIDA. Therefore, in order to isolate NPMG one needs to use either a large quantity of miscible organic solvent or to effect neutralization with base (leaving salt as an impurity in the NPMG). In both methods the isolation is not quantitive. In the third method one can use only a very dilute solution (N≈4% at 100° C.) of NPMIDA because of solubility problems. Therefore, to isolate the NPMG one needs to evaporate a large quantity of water. In order to overcome the solubility difficulties it would be better to directly oxidize the NPMIDS Salt that is more soluble than the acid.

Although U.S. Pat. No. 4,147,719 describes the direct oxidation of NPMIDA amine salts with oxygen and platinum on carbon, it is known that many amines may oxidize to a variety of products (such as: hydroxyl amine, nitroso, nitro, amine oxide, azoxy compound, oximes, hydroxamic acid and other combination products as well as hydrolysis products) when subjected to an oxidation reaction utilizing oxygen or hydrogen peroxide or may be dealkylated followed by oxidation to carbonyl or carboxylic acid derivatives when subjected to an oxidation reaction utilizing oxygen over a catalyst or Hydrogen Peroxide as oxidants (P.A.S. Smith, open chain nitrogen compound Vol. 1 page 47-50, 108-114, Benjamin, Inc. 1966; Houben-Weyl, Oxidation 4/1a page 72-168 and 293-315; G. Scott, Atmospheric Oxidation and Antioxidants page 198-203, Elsevier 1965; G. T. Davis and D. H. Rosenblatt, Tetrahydron Letter 4085 (1968) and R. D. Birkenmeyer and L. H. Dozak, Tetrahydron Letter 5049 (1970). Moreover the said patent (U.S. Pat. No. 4,147,719) claims that the presence of a formaldehyde coproduct in the oxidation of NPMIDA amine salts according to the following scheme

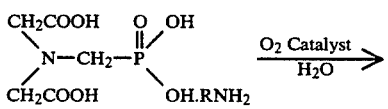

-continued
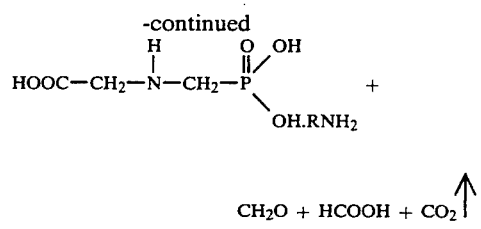

is undesired because formaldehyde may react with the NPMG product to produce an N-Methyl-N-Phosphonomethylglcine as by-product.

It is believed that the above by-product resulted from reductive methylation known in the art as Leuckart reaction or the closely related Eschweiler-Clarke methylation (Organic Reaction Vol V page 307 John Wiley & Sons 1949 New York) in which primary or secondary amine (as well as aminoacid) is heated with formaldehyde or preferably with formaldehyde and formic acid yielding methylated amine derivatives in good yield according to the reaction:

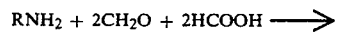
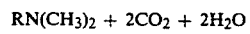

Therefore oxidation of an NPMG salt of primary or secondary amine may yield methylated amines as co product thus obtaining a mixture of NPMG amines salts instead of one sole product. Although said patent (U.S. Pat. No. 4,147,719) has found that using Pt/c as catalyst in the above oxidation can minimize or eliminate said phosphonic acid by-product nothing is said about the possibility of obtaining methylated amine by-products resulting from the said Leuckart reaction. Moreover, U.S. Pat. No. 4,147,719 does not describe the carrying out of any analysis of the amine cations of the NPMG salts obtained by the said oxidation and in fact said patent is directed to the production of the acid only and not to the direct production of amine salts as is the process of the present invention.

Therefore, the NPMG amine salts according to U.S. Pat. No. 4,147,719 will contain oxidation degradation and methylation products of the amines and some combination products of the above derivatives with the amino group of the NPMG (thereby also reducing the yield of active material). These by-products are difficult to separate from the desired product and therefore the oxidation solution cannot be used directly as a herbicide.

Receiving a pure product is highly important as this material is being used as a herbicide applied on human food and any residue is considered dangerous. While the effects of nitroso are today widely discussed, other combination trace products are not less important.

An experiment carried out by applicant to oxidize NPMIDA amines salts with $H_2O_2$ in aq. solution followed by addition of hydrochloric acid to precipitate the free NPMG resulted in a poor yield of NPMG together with a high percent of underfined by-products, thus further indicating the difficulties in obtaining a pure product by modification of the prior art processes.

Israel Specification No. 65187 now U.S. Pat. No. 4,397,676 takes advantage of the fact that iminourea derivatives are much more stable than amines toward oxidation and describes direct oxidation of NPMIDA iminourea salts using either O₂ over catalyst or Hydrogen Peroxide yielding NPMG iminourea salts. However some iminoureas e.g. 1-amino guanidine, diaminoguanidine, and the like may oxidize to a variety of products under the above condition. Moreover, the present novel invention affords a process for producing the NPMG sensitive iminourea salts as well as the other non-sensitive iminourea salts without subjecting the iminoureas to oxidation conditions.

With the above problems and state of the art in mind, it is the object of the present invention to provide a direct method for preparing pure NPMG salts, using H₂O₂ or oxygen over catalyst without subjecting the base forming cations (amines or iminourea) to the above oxidation conditions and in which method the formation of by-products is minimized and/or such by-products are easily isolated. This object is achieved by the present invention which, in contradistinction to the above-mentioned prior art processes provides a process for producing water-soluble mono and di-N-Phosphonomethylglycine amine and iminourea salt from N-phosphonomethyliminodiacetic acid derivatives comprising oxidizing an aryl substituted iminourea salt of N-phosphonomethyl iminodiacetic acid of the general formula VI

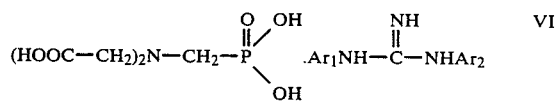

wherein $Ar_1$ and $Ar_2$ are each independently selected from the group consisting of phenyl, alkylphenyl and halophenyl to form a N-phosphonomethylglycine iminourea salt of the general formula VII

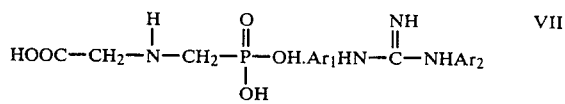

reacting said salt of formula VII with an amine, iminourea, diamine, or diiminourea having a molecular weight below 600 and a pKa above 10 in aqueous solution and separating the resulting water insoluble aryl iminourea from the resulting water soluble N-phosphonomethylglycine salt product.

More particularly, the present invention provides a process for producing N-phosphonomethylglycine derivatives of the general formula I

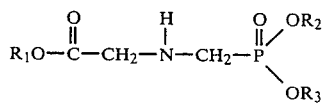

wherein,
a. $R_1$, $R_2$ and $R_3$ are independently selected from hydrogen and —$R_4$ and $R_4$ is a salt-forming cation iminourea derivative of the general formula II

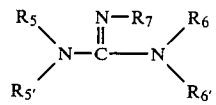

wherein $R_5$, $R_{5'}$, $R_6$, $R_{6'}$ and $R_7$ are independently H, $NH_2$, $CH_2OH$

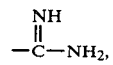

or an aryl, cycloalkyl or straight or branched chain alkyl or alkenyl group optionally substituted by hydroxy or halogen, or an alkylaryl group provided that
1. at least one but no more than two of $R_1$, $R_2$ or $R_3$ are $R_4$,
2. no more than one $R_5$, $R_{5'}$, $R_6$, $R_{6'}$ are aryl or substituted aryl; and
3. no more than one of $R_5$, $R_{5'}$, $R_6$, $R_{6'}$ and $R_7$ is $CH_2OH$; or b. $R_1$, $R_2$ and $R_3$ are independently selected from hydrogen and $R^{16}$ wherein $R^{16}$ is a salt-forming cation selected from the groups consisting of cations of organic ammonium selected from primary-, secondary- and tertiary-alkyl, none of these having more than two amine groups: and heterocyclic amines provided that no more than two of $R_1$, $R_2$ and $R_3$ are —$R^{16}$; or c. $R_1$ and $R_2$ are hydrogen and $R_3$ is $R_{17}$ wherein $R_{17}$ is a salt forming cation of the formula III

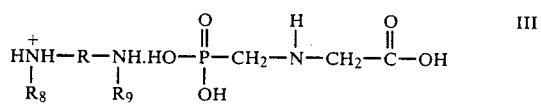

wherein R is selected from the group consisting of $C_2$-$C_{12}$ straight or branched chain alkylene radicals and $R_8$ and $R_9$ are each independently H or a $C_1$-$C_4$ alkyl group: or d. $R_1$ and $R_2$ are H and $R_3$ is a salt forming cation of the general formula IV

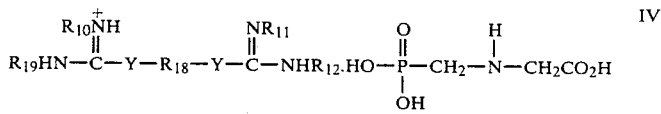

wherein Y is N, $R_{18}$ is a straight or branched chain alkylene radical having 1-12 carbon atoms and $R_{19}$, $R_{11}$, $R_{12}$ and $R_{10}$ are each independently H, alkyl, phenyl or allyl provided that only one of $R_{19}$ and $R_{10}$ may be alkyl, allyl or phenyl and only one of $R_{11}$ and $R_{12}$ may be alkyl, allyl or phenyl;

said process comprising oxidizing an aryl substituted iminourea salt of N-phosphonomethyliminodiacetic acid of the general formula VI

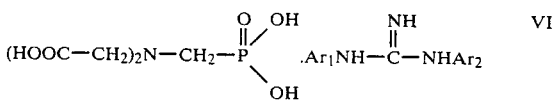

wherein $Ar_1$ and $Ar_2$ are each independently selected from the group consisting of phenyl, alkylphenyl and halophenyl to form a N-phosphonomethylglycine iminourea salt of the general formula VII

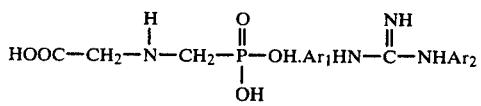

and then reacting said salt of formula VII with the appropriate amine, iminourea, diamine or diiminourea as defined.

Preferably at the end of said process the resulting NPMG salt solution is separated by filtration from the regenerated aryl-substituted iminourea which iminourea is purified and recycled for use in the preparation of the salt of formula VI thereby resulting in a simple economical process which not only produces relatively pure N-Phosphonomethylglycine salts using a direct oxidation process without the drawbacks of the prior art processes but also results in the regeneration for reuse and substantially without loss, of the aryl substituted iminourea reactant which makes the process feasible and practical.

As stated above, the iminourea salts of the above salts are those prepared from low molecular weight iminourea, i.e. having a molecular weight below about 600 and a $P^{Ka}$ above 10.0, such as: Guasnidine, 1-amino guanidine, N,N'-diamino guanidine, biguanide, methyl guanidine, dimethyl guanidine, trimethyl guanidine, ethyl guanidine, diethyl guanidine, triethyl guanidine, tetra methyl guanidine, tetra ethyl guanidine, penta methyl guanidine, phenyl guanidine, N,N'-ethylene diguanidine, N,N'-propylene diguanidine, N,N'-butylene diguanidine. The organic ammonium salts of the above salts are those prepared as above from low molecular weight amine, i.e., having a molecular weight below about 300 and their pKa are above 10.0 such as: methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-secbutylamine, tri-n-amylamine, ethanolamine, n-propanolamine, N,N-diethylethanolamine, N-ethylpropanolamine, ethylene diamine, propylenediamine, N-ethyl-ethylenediamine, N-Methyl-ethylenediamine, 2-Methyl, 1-2-propylene diamine, N,N,N,N'-tetra ethyl-1,3-propylenediamine, 1,4-diaminobutane and the like and hetrocyclic amines such as piperidine, pyrolidine and the like.

In a preferred embodiment of the present invention the salts of general formula VI are first prepared by forming an admixture of N-Phosphonomethyl Imino diacetic acid and an aryl substituted Imino urea preferably selected from the group consisting of N, N' diphenyl guanidine, N,N' di-o-tolyl guanidine, N,N'-di-p-toly guanidine, N,N'-di-4-ethyl phenyl guandine, N,N'-di-4-chlorophenyl guanidine and N,N'-di- 4-bromo phenyl guanidine and heating the mixture until a clear solution is obtained.

Thus each of said aryl groups is preferably phenyl, totyl, bromophenyl or chlorophenyl.

All of said Di-Aryl Imino Ureas are practically water insoluble and have $P^{Ka}$ lower than 10.1.

In conducting the oxidation processes the temperature of reaction can be from as low as 20° C. to 125° C. or even higher. It is preferred, for ease of reaction and to obtain the best yield of product, to conduct said processes at from about 70° C. to about 120° C.

The time of reaction is not narrowly critical and can vary from 15 minutes heating time to as high as 40 or more hours. Of course, it is obvious to those skilled in the art that the yield of the product will vary with the reaction time and the temperature of the reaction.

The process is carried out in an aqueous media. It is preferred to employ a saturated solution of N-(Phosphonomethyl) iminodiacetic salt in water. However, for ease of operation, the process is also operable at lower or higher concentration in water.

The ratio of reactants, that is the oxidizing agent and the N-(Phosphonomethyl) iminodiacetic acid (NPMIDA) salt is not narrow. For best yields one should employ at least a stoichiometric amount of oxidizing agent, e.g. 2 mole Hydrogen Peroxide and ½ of $O_2$ for each equivalent of N-(Phosphonomethyl) iminodiacetic salt. In actual practice, however, to obtain the best yields, one employs 3-4 mole of Hydrogen Peroxide and ½ to 1 mole of oxygen for each mole NPMIDA salts. When a free oxygen-containing gas is employed it is preferred for convenience to conduct the process of this invention at a total pressure of from 0.5 $kg/cm^2$ to 200 $kg/cm^2$. It is even more preferred to conduct said process at pressure of from 1 $kg/cm^2$ to 5 $kg/cm^2$.

The manner in which the aqueous solution of the Iminodiacetic acid salts (NPMIDA) is contacted with the molecular oxygen containing gas and catalyst (activated carbon or metal catalyst) can vary greatly. For example the Iminodiacetic acid salts solution can be placed in closed container with some free space containing molecular oxygen and shaken vigorously or agitated by stirring or molecular oxygen containing gas can be bubbled through a straight tube or a tube with a fritted diffuser attached thereto. The contacting can also be accomplished in a tubular continuous reactor packed with activated carbon.

The oxidizing agent which can be employed to prepare the compounds of the present invention include oxidizing agents such as inorganic peroxides, including Hydrogen Peroxide and organic peroxides. The organic peroxide oxidizing agents include: Performic acid, Peracetic acid, Perbenzoic acid and the like.

Other inorganic oxidizing agents include oxygen, air, oxygen diluted with helium, argon, nitrogen or other inert gas in the presence of catalysts such as:

activated carbon, metallic catalysts (Pt, Pd, Rh, Ru, etc.) alone or on activated supports such as activated charcoal, aluminum oxide, asbestos etc.

The activated carbon catalysts employed are characterized by high adsorptive capacity for gases, vapors and colloidal solids and relatively high specific surface areas. The specific surface area of the activated carbon can be from 100-2000 square meters per gram. It is preferred to employ activated carbons having a specific surface area of 400 to 1600 square meters per gram.

The activated carbons employed in said process can be in the form of powders or granules. In the powder form the activated carbons consist largely of material having a particle size finer than 325 mesh although some larger particles may also be present in the granular form. The particle size range can vary considerably, particle size of 4×10 mesh, 8×30 mesh and 20×30 mesh can be used.

The amount of granular or powdered activated carbon employed in this process can range from 0.5 to 100 or more parts by weight for every 100 parts by weight of NPMIDA salt employed.

As will be realized, the form of the activated carbon, its pH and its area, all effect the rate of the reaction of the NPMIDA salts with oxygen in this process. Experiments indicate that the reaction rate is faster when the active carbon was washed with concentrated hydrochloric acid and then washed with water (up to pH=7) before use.

Some examples of activated carbon are: Norit PN-4, Norit A, Norit ACX (Amer. Norit Co., Inc., Jacksonville, Fla.), Darco 6-60 (ICI-America), grade 235 and 256 (Witco Chemical Corp), Columbia SXAC (Union Carbide) and the like.

The metal on support catalyst are the commercial 5% metal on activated carbon such as 5% Pd/c, 5% Rh/c, 5% Pt/c, 5% Pt/Al$_2$O$_3$ and 5% Rh/Al$_2$O$_3$.

The reaction between amines or iminourea and the salt of general formula VII is conducted at room temperature in water by adding two moles of the base to one mole of the salt of formula VII in water and stirring the mixture for ½ hour whereafter the water insoluble iminourea and its by product is filtered. The filtrate contain Pure NPMG Di Basic Salts.

In order to obtain monobasic NPMG salts from said Di Basic NPMG salt, one can add one mole NPMG, produced by neutralization of salt VII with hydrochloric acid, to the solution of said di basic salt.

The Di-Aryl iminourea canb be isolated from its hydrochloride salt by neutralization with sodium hydroxide followed by filtration.

Thus, e.g., the reaction between isopropyl amine and the salt of general formula VII is conducted at room temperature in water by adding the stochiometric amount of the IPA to the aq solution of the salt of formula VII and stirring the mixture for ½ hour whereafter the water insoluble iminourea and its by product is filtered. The filtrate contain Pure NPMG (IPA)$_2$ Salt.

In order to obtain monoisopropyl NPMG from said di-isopropyl amine NPMG salt, one can add one mole NPMG, produced by neutralization of said di-salt with hydrochloric acid, to the solution of said di-salt according to the following reaction scheme

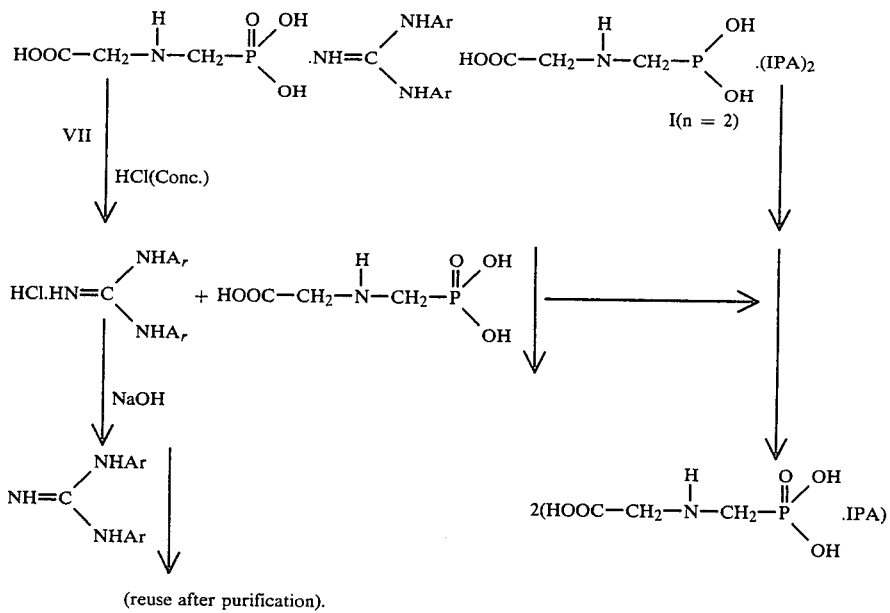

(reuse after purification).

The iminourea can be isolated from its hydrochloride salt by neutralization with sodium hydroxide followed by filtration.

It is worthwhile to emphasize the following additional advantage of the present invention:

Formaldehyde is not produced as coproduct in the oxidation of the salt of general formula VI with Hydrogen Peroxide thus N-Methyl-N-Phosphonomethyl glycine coproduct previously discussed is not formed through reductive alkylation. The oxidation of the above salt VI utilizing oxygen over a catalyst yielded formaldehyde as by product, however, it is known in the art that ureas and iminoureas are good formaldehyde scavenging agents [(U.S. Pat. No. 3,957,431 and H. A. Fraenkel and H. S. Olcott, J. Amer. Chem. Soc., 68, 34–7 (1976)] therefore the Di-Aryl Iminourea in Salt VI can minimize the formation of N-Methyl NPMG co-product by scavenging some of the formaldehyde. On the other hand, the said Leuckart reductive Methylation fails with compounds such as amides, urea and iminourea thus no reductive methylation of said Di-aryl iminourea takes place (Organic Reaction Vol V Page 308, John Wiley & Sons 1949 New York).

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

In the following examples which illustrated the invention and throughout the specification, parts and percent are by weight unless otherwise indicated.

EXAMPLE 1

A series of runs were made to oxidize N-(Phosphonomethyl) Iminodiacetic Iminourea Salts using $H_2O_2$ as oxidant.

Forty parts of water and 0.02 mole of NPMIDA Salt were charged into a suitable reactor. The mixture was heated to 80° C. and then 8.8 parts of 30% $H_2O_2$ was added over a period of 1 to 2 hours while maintaining the temperature at 70° C. The reaction was then heated at 80° C. with stirring until Nuclear Magnetic Resonance spectral (NMR) analysis showed that the reaction was essentially complete. The reaction was terminated, excess $H_2O_2$ was decomposed by activated carbon, the carbon was filtered off leaving a clear solution of NPMG Iminourea Salt which was subject to NMR analysis.

The following table gives the result of these experiments.

| EXPERIMENT NO. | IMINOUREA | REACTION TIME | MOLE % NPMG SALT | MOLE % NPMIDA SALT |
| --- | --- | --- | --- | --- |
| 1 | DPG | 4.5 | 100 | 0 |
| 2 | DTG | 4.5 | 97 | 3 |
| 3 | DPG | 4 | 97 | 3 |
| 4 | CDPG | 5 | 98 | 2 |

DPG — N, N'—Di Phenyl Guanidine
DTG — N, N'—Di-o-Tolyl Guanidine
CDPG — N, N'—Di 4-chlorophenyl guanidine

EXAMPLE 2

A series of runs were made to oxidize N-(Phosphonomethyl) Iminodiacetic imino urea salt using oxygen as oxidant. This series was conducted in a low pressure apparatus consisting of a Parr shaker to provide agitation. The following table gives the result of these experiments. In these experiments 0.5–1 grams of catalyst, 0.02 mole of NPMIDA Salt and 40 g of distilled water were charged into the bottle and heated to 90° C. the bottle was sealed, placed in the shield and alternately pressurized and depressurized several times with $O_2$ gas at 1–3 kg/$cm^2$ to remove the air. The reactions were all conducted at 3–1 kg/$cm^2$. After the reaction was terminated the catalyst was filtered off and the filtrate was subject to NMR analysis.

| EXPERIMENT NO. | IMINOUREA | CATALYST | PRESSURE | TIME | MOLE % NPMG | MOLE % NPMIDA |
| --- | --- | --- | --- | --- | --- | --- |
| 5 | DPG | Norit PN—3,1.0 g | 1 | 10 | 100 | — |
| 6 | DPG | 5% Rh/c,1.0 g | 2 | 2.5 | 100 | — |
| 7 | DPG | 5% Pt/c,1.0 g | 2 | 3 | 98 | 2 |
| 8 | DTG | Norit A,1.0 g | 2.1 | 2 | 90 | 10 |
| 9 | DTG | Norit PN—3,1.0 g | 1 | 10 | 95 | 5 |
| 10 | DTG | 5% Pt/c,1.0 g | 2.1 | 2.5 | 100 | — |
| 11 | DPG | Norit A,1.0 g | 1 | 10 | 98 | 2 |
| 12 | DPG | 5% Pt/c,0.5 g | 2.1 | 3 | 98 | 2 |
| 13 | CDPG | Norit PN—3,1.0 g | 1 | 10 | 99 | 1 |
| 14 | CDPG | 5% Pt/c,0.5 g | 2.1 | 3 | 98 | 2 |

EXAMPLE 3

General procedures for preparing Mono and Di Basic salts of NPMG.

A solution of NPMG-N,N'Di Aryl guanidine Salt (0.02 mole in 40 ml $H_2O$) obtained either from example 1 or 2 and 0.04 mole of the base (amine or iminourea) was agitated in a suitable vessel at 25° C.

A precipitate of DPG was separated immediately and the agitation of the mixture was continued for ½ hour. The DPG was filtered and dried (yielding 4.15 g, approximately 0.02 mole) and the filtrate was found to contain pure NPMG di-Basic salt (through NMR analysis).

B. A solution of NPMG—N,N'—Di Aryl Guanidine salts (0.02 mole in 40 ml $H_2O$ obtained either from example 1 or 2 and Hydrochloric acid (0.02 mole, 2.22 g 32%) was agitated in a suitable vessel at 20° C. After a few minutes a precipitate of NPMG was separated. The NPMG was filtered and dried. 0.02 mole of aq NPMG—Di Basic salt obtained in A was added to 0.02 mole NPMG (obtained above) and the mixture was agitated until a clear solution was obtained. The solution was found to contain pure NPMG-Mono Basic Salt (through N.M.R. analysis).

Following the above procedure the following amine and diamine salts of NPMG can be prepared, e.g. Mono and Di(methyl amine) salts, Mono and di(ethylamine) salts, Di(dimethyl amine) salts, Mono and di(trimethyl amine) salts, Mono and Di(propylamine) salts, di(isopropylamine) salts, Mono and di (triethylamine) salts, Mono and di(butyl amine) salts, Mono and di (sec-butyl amine) salts, Mono and di(ethanol amine) salts, Mono and di(dimethyl ethyl amine) salts, Mono and di (ethylene diamine) salts, Mono and di (1,2 propylene diamine) salts, Mono nd di(N,N-diethyl-3-propylenediamine) salts, Mono and di (1,4-Diamino Butane) salts and the like.

Following the above procedure the following iminourea and diiminourea salts of NPMG can be prepared e.g. Di (aminoguanidine) salts, Mono and di (diaminoguanidine) salts, Mono and di (methyl guanidine) salts, di (tetramethyl guanidine) salts, Mono and di (ethylene diguanidine) salts, Mono and di (propylene diguanidine) salts and the like.

EXAMPLE 4

General procedures for preparing Mono (diamine) di-NPMG or Mono (diiminourea) di-NPMG salts III.

NPMG (0.06 mole, 102 gr) obtained as in example 3A was added to a solution of di (diamine) or di (diiminourea) salt of NPMG (0.02 mole in 50 ml water) obtained as in example 3B. The mixture was agitated until a clear solution was obtained. The solution was found to contain pure Mono (diamine) or Mono (diiminourea) di-NPMG salt (through NMR analysis).

Following the above procedure the following diamine and diiminourea salts of NPMG can be prepared e.g., Mono (1,3-propylenediamine) di-NPMG, Mono (N,N-diethyl 1,3-propylene diamine) di-NPMG, Mono (1,4-diamino butane) di-NPMG, Mono (ethylene diguanidine) di-NPMG, Mono (Propylene di-guanidine) di-NPMG and the like.

Other compounds of the present invention that can be made in general accordance with the foregoing procedures include:

(a) the mono-di Methyl amine salt of NPMG as a white solid m.p. 150° C. with decomposition.
(b) the mono isopropylamine Salt of NPMG NMR ($D_{2O}$, δppm, relative to HOD): −3.6 (d,6H, J=6H$_z$); 1.7 (d,2N, J=13H$_z$); −1.22 (3H).
(c) the Di (Guanidine) Salt of NPMG as a white solid.
(d) the Mono-Guanidine Salt of NPMG, white solid, m.p. −218°-220° (Dec.)
(e) the mono-tetramethyl guanidine salt of NPMG as a white deliquest solid m.p. 175°-6° C. (dec). NMR ($D_2O$, δ ppm, relative to HOD): −1.23 (S,2H): −1.73 (d, 2H, J=13H$_z$): −2.03 (S, 12H, CH$_3$);
(f) the Di-NPMG Ethylene diamine salt NMR ($D_2O$, δ ppm, relative to HOD): −1.8 (d,4H, J=13H$_z$): −1.9 (S,4H): −1.33 (S,4H);
(g) the di-NPMG 1,2-propylene diamine salt m.p. 92°-94° C. with evolution of bubbles; and
(h) the monoaminoguanidine salt of NPMG as a very deliquest white solid. m.p. −80° (dec.) (yield=95%) NMR ($D_2O$, δppm, relative to HOD); −1.17 (S,2h); −1.64(d,2H,J=13H$_z$).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come with the meaning and range of equivalency of the claims are therefore intended to be embraced therein.

What is claimed is:

1. A process for producing water-soluble mono and di-N-Phosphonomethylglycine amine and iminourea salts from N-phosphonomethyliminodiacetic acid derivatives comprising oxidizing an aryl substituted iminourea salt of N-phosphonomethyliminodiacetic acid of the formula VI

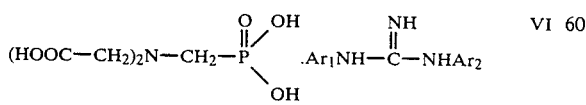

wherein Ar$_1$ and Ar$_2$ are each independently selected from the group consisting of phenyl, alkylphenyl and halophenyl to form a N-phosphonomethylglycine iminourea salt of the formula VII

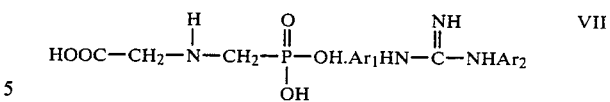

reacting said salt of formula VII with an amine, iminourea, diamine, or diiminourea having a molecular weight below 600 and a pKa above 10 in aqueous solution and separating the resulting water insoluble aryl iminourea from the resulting water soluble N-phosphonomethylglycine salt product.

2. A process according to claim 1 for producing N-phosphonomethylglycine derivatives of the formula I $$R_1O-\overset{O}{\underset{\|}{C}}-CH_2-\overset{H}{\underset{|}{N}}-CH_2-\overset{O}{\underset{\|}{P}}\diagdown\overset{OR_2}{\underset{OR_3}{}}\quad I$$

wherein
(a) R$_1$, R$_2$ and R$_3$ are independently selected from hydrogen and —R$_4$ and R$_4$ is a salt-forming cation iminourea derivative of the formula II $$\underset{R_{5'}}{\overset{R_5}{\diagdown}}N-\overset{N-R_7}{\underset{\|}{C}}-N\underset{R_{6'}}{\overset{R_6}{\diagup}}\quad II$$

$$\underset{R_{5'}}{\overset{R_5}{\diagdown}}N-\overset{N-R_7}{\underset{\|}{C}}-N\underset{R_{6'}}{\overset{R_6}{\diagup}}\quad II$$

wherein R$_5$, R$_{5'}$, R$_6$, R$_{6'}$ and R$_7$ are independently H, NH$_2$, CH$_2$OH or an aryl, cycloalkyl or straight or branched chain alkyl or alkenyl group optionally supstituted by hydroxy or halogen, or an alkylaryl group provided that
1. at least one but no more than two of R$_1$, R$_2$ or R$_3$ are R$_4$,
2. no more than one R$_5$, R$_{5'}$, R$_6$, R$_{6'}$, are aryl or substituted aryl; and
3. no more than one of R$_5$, R$_{5'}$, R$_6$, R$_{6'}$, and R$_7$ is CH$_2$OH; or (b) R$_1$, R$_2$ and R$_3$ are independently selected from hydrogen and R$^{16}$ wherein R$^{16}$ is a salt-forming cation selected from the groups consisting of cations of organic ammonium selected from primary-, secondary- and tertiary-alkyl, none of these having more than two amine groups; and heterocyclic amines provided that no more than two of R$_1$, R$_2$ and R$_3$ are —R$^{16}$; or (c) R$_1$ and R$_2$ are hydrogen and R$_3$ is R$_{17}$ wherein R$_{17}$ is a salt forming cation of the formula III $$\overset{+}{H}NH-\underset{R_8}{\overset{}{R}}-NH.HO-\overset{O}{\underset{\|}{P}}-CH_2-\overset{H}{\underset{|}{N}}-CH_2-\overset{O}{\underset{\|}{C}}-OH\quad III$$
$$\underset{R_9}{}\quad\underset{OH}{}$$

wherein R is selected from the group consisting of C$_2$-C$_{12}$ straight or branched chain alkylene radicals and $R_8$ and $R_9$ are each independently H or a $C_1$-$C_4$ alkyl group; or (d) $R_1$ and $R_2$ are H and $R_3$ is a salt forming cation of the formula IV

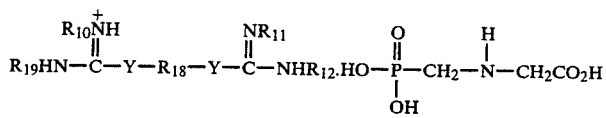

IV

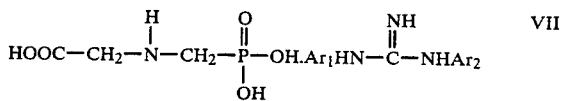

VII wherein Y is N, $R_{18}$ is a straight or branched chain alkylene radical having 1-12 carbon atoms and $R_{19}$, $R_{11}$, $R_{12}$ and $R_{10}$ are each independently H, alkyl, phenyl or allyl provided that only one of $R_{19}$ and $R_{10}$ may be alkyl, allyl or phenyl and only one of $R_{11}$ and $R_{12}$ may be alkyl, allyl or phenyl;

said process comprising oxidizing an aryl substituted iminourea salt of N-phosphonomethyliminodiacetic acid of the formula VI

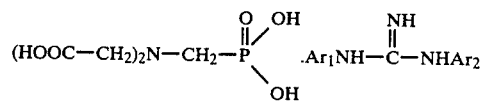

wherein $Ar_1$ and $Ar_2$ are each independently selected from the group consisting of phenyl, alkylphenyl and halophenyl to form a N-phosphonomethylglycine iminourea salt of the general formula VII and then reacting said salt of formula VII with the appropriate amine, iminourea, diamine or diiminourea as defined.

3. A process according to claim 1 wherein the resulting NPMG salt solution is separated by filtration from the regenerated aryl-substituted iminourea which iminourea is purified and recycled for use in the preparation of the salt of formula VI.

4. A process according to claim 1 wherein said oxidation is carried out using hydrogen peroxide as an oxidizing agent.

5. A process according to claim 1 wherein said oxidation is carried out using a molecular oxygen-containing gas in the presence of a metal or activated carbon catalyst.

6. A process according to claim 1 wherein the salts of formula VI are first prepared by forming an admixture of N-phosphonomethyliminodiacetic acid and an imino urea selected from the group consisting of N, N' diphenyl guanidine, N,N'di-o-tolyl guanidine; N,N'-di-p-tolyl guanidine, N,N'-Di-4-Ethyl phenyl guanidine, N,N'-Di-4-Chloro phenyl guanidine and N,N'-di-4-bromo phenyl guanidine and heating the mixture until a clear solution is obtained.

7. A process according to claim 1 wherein said oxidation is carried out at a temperature of about 70° to about 120° C.

* * * * *